United States Patent [19]

Jessen

[11] Patent Number: 5,192,289

[45] Date of Patent: Mar. 9, 1993

[54] ANASTOMOSIS STENT AND STENT SELECTION SYSTEM

[75] Inventor: John W. Jessen, Seattle, Wash.

[73] Assignee: Avatar Design and Development, Inc., Seattle, Wash.

[21] Appl. No.: 814,328

[22] Filed: Dec. 23, 1991

Related U.S. Application Data

[63] Continuation of Ser. No. 689,669, Apr. 23, 1991, abandoned, which is a continuation of Ser. No. 320,983, Mar. 9, 1989, abandoned.

[51] Int. Cl.⁵ ............................................. A61B 17/00
[52] U.S. Cl. .................................... 606/155; 606/153; 623/12
[58] Field of Search ............... 606/153, 154, 155, 156; 623/12

[56] References Cited

U.S. PATENT DOCUMENTS

| | | | |
|---|---|---|---|
| 2,127,903 | 8/1938 | Bowen | 128/334 R |
| 3,044,497 | 7/1962 | Rebut | 128/334 R |
| 3,221,746 | 12/1965 | Noble | 128/334 R |
| 3,683,926 | 8/1972 | Suzuki | 128/334 R |
| 3,815,578 | 6/1974 | Bucalo | 128/334 R |
| 4,674,506 | 6/1987 | Alcond | 606/653 |
| 4,705,039 | 11/1987 | Sakaguchi et al. | 128/334 C |
| 4,753,236 | 6/1988 | Healey | 128/334 R |

Primary Examiner—Stephen C. Pellegrino
Assistant Examiner—Gary Jackson
Attorney, Agent, or Firm—Christensen, O'Connor, Johnson & Kindness

[57] ABSTRACT

A stent or support is disclosed for use in the connection or anastomosis of severed vessels to support and seal the anastomotic site. The stent includes substantially cylindrical sections separated by a tapered transitional region. The cylindrical sections are provided with flanges that define tapered sealing surfaces. The dimensions of the two sections are selected to correspond with the diameter of the portions of the vessel to be supported. The stent is preferably made of polyglycolic acid and the dimensions of the stent are selected to provide optimal support and sealing characteristics with a minimum of damage to the epithelial lining of the vas deferens. In two preferred applications, the stent is used in anastomosis of the severed ends of a vas deferens and a Fallopian tube. A gauge is used to measure the severed ends and, in that manner, determine the appropriate dimensions of the stent.

12 Claims, 3 Drawing Sheets

ANASTOMOSIS STENT AND STENT SELECTION SYSTEM

This application is a continuation application based on prior copending application Ser. No. 689,669, filed on Apr. 23, 1991, now abandoned, which, in turn, was a continuation application based on prior copending application Ser. No. 320,983, filed on Mar. 9, 1989, now abandoned.

FIELD OF THE INVENTION

This invention relates generally to stents and, more particularly, to stents for use in anastomosis.

BACKGROUND OF THE INVENTION

Fluid-carrying vessels exist in a wide number of systems, including those physiological systems found, for example, in the human body. The assembly, modification, or repair of such systems frequently involves the connection or anastomosis of two or more vessels to define a fluid path. To assist in anastomosis of physiological vessels, an internal support or stent may be employed at the vessel junction. The stent maintains the desired orientation of the vessels and provides rigidity to the vessels at the point of connection, or anastomotic site. In addition, the stent may reduce leakage at the anastomotic site by by confining the fluid to a passage extending through the stent.

Given the nature of physiological vessels, their connection frequently requires the use of a stent only until the vessel tissue reorganizes to provide a continuous, healed conduit. One stent designed to provide such temporary support to physiological vessels is described in U.S. Pat. No. 3,620,218. There, a cylindrical support made of polyglycolic acid is disclosed for use in connecting a variety of vessels including blood vessels, spermatic ducts, bile ducts, ureters and sinus tubes. This internal support is located at the anastomotic site and supports the vessel ends, which are held together by sutures or clamps of polyglycolic acid. In one embodiment, the support has tapered ends to make insertion into the vessel ends easier. In another embodiment, the ends are slightly expanded to hold the vessels in place about the support. The reference also notes that the diameter of the support may vary where vessels of different size are to be spliced.

While prior art supports have aided in the connection of physiological vessels, several problems may still be encountered. First, because a physiological vessel is a relatively sensitive structure, it can be easily damaged by a support arrangement that applies pressure to fixed portions of the vessel for extended periods. Further, when vessels of varying diameter are to be joined, the sharp transition in diameter at the anastomotic site may lead to puckering of the vessel ends and misalignment of the joined vessels. Finally, the ability of a particular support to be inserted into, and seal, a vessel may vary significantly with even minor variations in vessel size. In light of these observations, it would be desirable to produce an anastomosis stent that does not significantly injure the vessel, that allows a good connection to be produced between vessels of different size, and that is dimensioned to produce optimal insertion and sealing characteristics when used with the particular vessels to be joined.

SUMMARY OF THE INVENTION

In accordance with this invention, a stent is provided for use in the reconnection of a severed vessel that may carry fluid and that has a first free portion and a second free portion. The stent includes a support for supporting the first and second portions of the vessel. Flanges are also provided on the support for sealably engaging the first and second portions of the vessel. The flanges sealably engage the first and second portions of the vessel in a manner that varies with use of the stent to minimize trauma to the vessel.

BRIEF DESCRIPTION OF THE DRAWINGS

The invention will presently be described in greater detail, by way of example, with reference to the accompanying drawings, wherein.

DETAILED DESCRIPTION OF THE PREFERRED EMBODIMENT OF THE INVENTION

Figure 1:
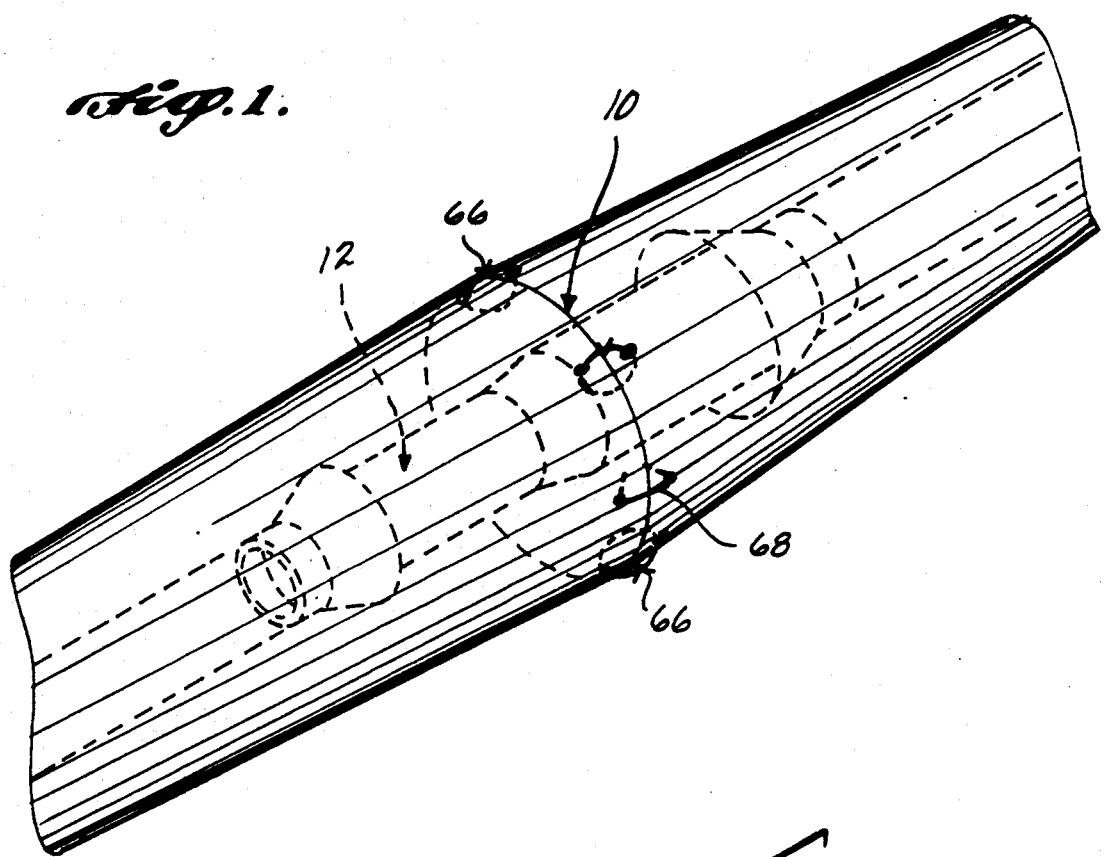
FIG. 1 is a pictorial view of the anastomotic site of a reconnected vas deferens, supported by a stent constructed in accordance with this invention.

Referring now to FIG. 1, an anastomotic site 10, supported by a hollow stent 12 constructed in accordance with this invention, is shown. While the connection of fluid-carrying vessels in numerous physiological systems can be supported in this manner, in the preferred embodiment, the stent 12 is constructed for use at the anastomotic site 10 produced by the surgical procedure known as a vasovasostomy. Before describing stent 12 in greater detail, a brief outline of this surgical procedure is provided.

Briefly, a vasovasostomy is the reversal of an earlier surgical procedure known as a vasectomy, which is used for male sterilization. In a vasectomy, a small section of the vas deferens is surgically removed and the proximal and distal ends leading from the testicle and to the abdomen, respectively, are cauterized and tied. In a vasovasostomy this process in reversed by surgically reconnecting the severed ends of the vas deferens. The testicular portion always swells an unknown, variable amount after being tied. Thus, a surgeon performing a vasovasostomy is faced with the problem of joining vessels of differing diameters.

As will be appreciated, the success of this procedure depends on a number of considerations. For example, if the tissue of the vas deferens is to reorganize normally, it must be maintained in close contact during healing. In addition, the anastomotic site must not be allowed to collapse or the passage of sperm through the vas deferens will be blocked. To increase the likelihood of success, the stent 12 is inserted into the severed ends of the vas deferens during the vasovasostomy to support the anastomotic site during tissue recombination. In this manner, the desired alignment of the vas deferens is maintained during healing and the anastomotic site is prevented from collapsing.

Figure 2:
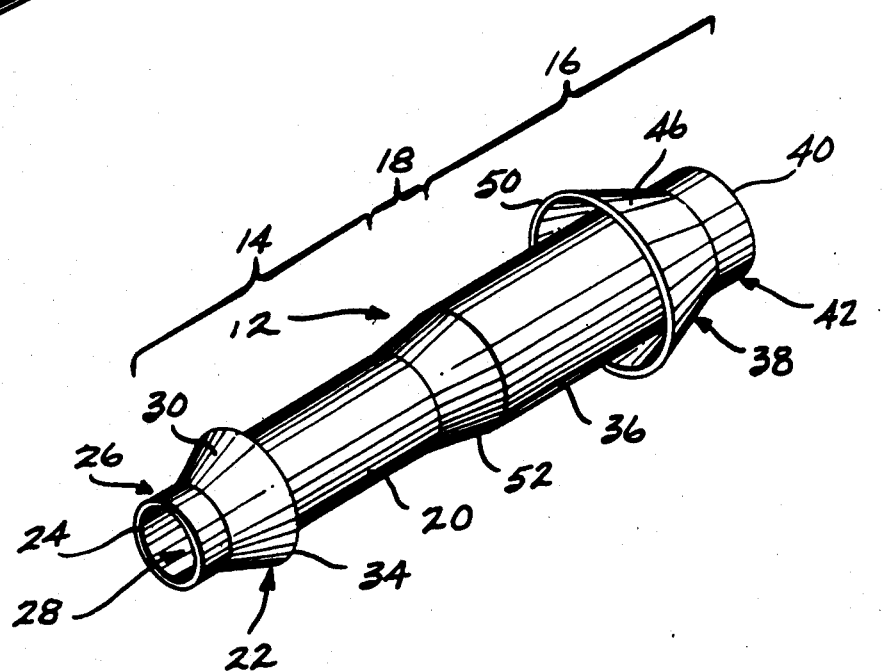
FIG. 2 is a pictorial view of the stent employed at the anastomotic site of FIG. 1.
Figure 3:
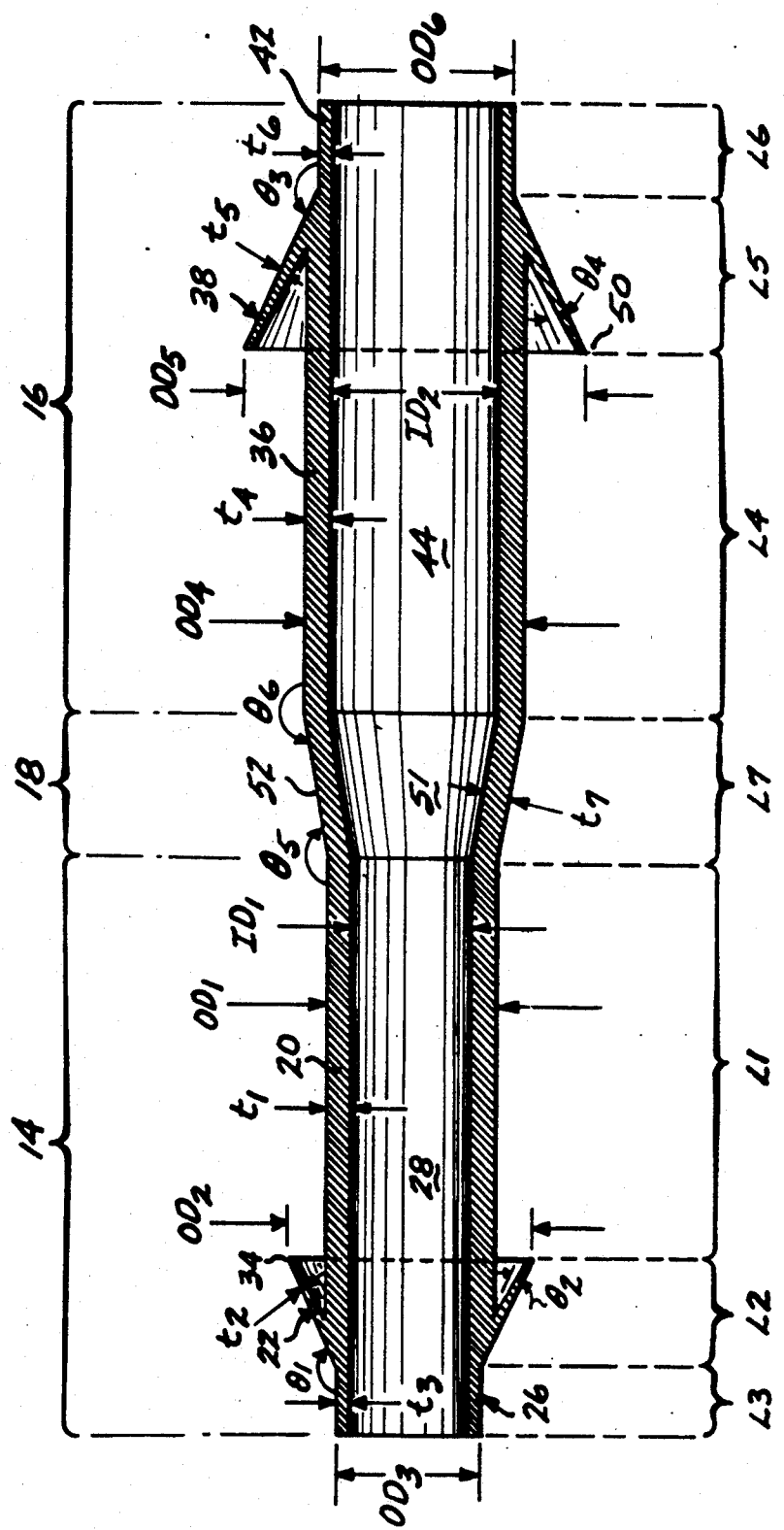
FIG. 3 is a longitudinally sectioned view of the stent of FIG. 2.

Turning now to a detailed consideration of stent 12 and the advantages of its construction, reference is made to FIGS. 2 and 3. As shown, stent 12 can be roughly divided into three sections. A first section 14 is structured to support and sealably engage the abdominal (distal) portion of the vas deferens. A second section 16 is constructed to sealably engage and support the testicular (proximal) portion of the vas deferens. A third section 18, located intermediate the first and second sections 14 and 16, is designed to support the anastomotic site and provide a smooth transition between the larger proximal and smaller distal portions of the vas deferens.

Referring now to the first section 14, as shown in FIGS. 2 and 3, it includes a cylindrical body portion 20 having a sealing flange 22 that is spaced apart from the distal end 24 of stent 12 by a cylindrical end portion 26. The body portion 20 is hollow, having a coaxial cylindrical passage 28 extending therethrough. As described in greater detail below, the body portion 20 has an outer diameter $OD_1$, an inner diameter $ID_1$, a thickness $t_1$, and a length $L_1$, particularly dimensioned for use with the distal portion of the vas deferens.

Turning now to a discussion of flange 22, flange 22 generally resembles the frustum of a cone whose reduced-diameter end is oriented proximal the end portion 26 of stent 12. As shown in FIG. 3, the flange 22 is undercut. Flange 22 includes an exposed sealing surface 30 that defines an obtuse angle $\theta_1$ with the cylindrical end portion 26 of stent 12 and that terminates in an outer rim 34. The inner surface of the flange 22 is tapered at an angle $\theta_2$, causing its thickness $t_2$ to decrease as the rim 34 is approached. The flange 22 has a first outer diameter $OD_2$ at rim 34 and a second outer diameter $OD_3$ at the end of flange 22 adjacent end portion 26. Flange 22 has a length $L_2$.

The final portion of section 14 of stent 12 to be considered is the cylindrical end portion 26, located between the distal end 24 of stent 12 and the flange 22. As shown in FIG. 3, end portion 26 has an outer diameter $OD_3$ and an inner diameter $ID_1$ defined by cylindrical passage 28. End portion 26 further has a wall thickness $t_3$ and a length $L_3$.

Addressing now the details of the second section 16 of stent 12, its structure corresponds to that of first section 14. More particularly, second section 16 includes a cylindrical body portion 36 having a sealing flange 38 that is spaced apart from the testicular (proximal) end 40 of stent 12 by a cylindrical end portion 42. The body portion 36 has an outer diameter $OD_4$ and an inner diameter $ID_2$, which is defined by a coaxial cylindrical passage 44. The body portion 36 also has a wall thickness $t_4$ and a length $L_4$.

Turning now to a description of flange 38, its general shape is that of the frustum of a cone whose reduced-diameter end is oriented proximal the end portion 42 of stent 12. Flange 38 is undercut and includes an exposed sealing surface 46 that defines an obtuse angle $\theta_3$ with the cylindrical end portion 42. The inner surface of flange 38 is tapered at an angle $\theta_4$, causing the thickness $t_5$ of flange 38 to decrease as the outer rim 50 of flange 38 is approached. As shown in FIG. 3, the flange 38 has an outer diameter $OD_5$ at rim 50 and an outer diameter $OD_6$ adjacent end portion 42. Flange 38 has a length $L_5$.

The end portion 42 of the second section 16 of stent 12 extends between flange 38 and the testicular end 40 of stent 12. The end portion 42 has an outer diameter $OD_6$ and an inner diameter $ID_2$ that is defined by a coaxial cylindrical passage 44. The wall thickness of end portion 42 is designated $t_6$, while its length is designated $L_6$.

Turning now to a discussion of the third section 18 of stent 12, as shown in FIGS. 2 and 3, section 18 joins the first and second sections 14 and 16 of stent 12 and is shaped substantially like the frustum of a cone. More particularly, it includes a tapered fluid passage 51 and tapered transitional support surface 52 that defines an obtuse angle $\theta_5$ with the surface of the cylindrical body portion 20 of first section 14. Given the axial alignment of the first and second sections 14 and 16, transitional surface 52 defines an angle $\theta_6$ with the surface of the cylindrical body portion 36 of the second section 16 that is equal to 360 degrees minus $\theta_5$. The thickness of the third section is designated $t_7$ and its length is designated $L_7$.

Having briefly reviewed the structure of stent 12, its role in the performance of a vasovasostomy will now be considered. The first section 14 and second section 16 are inserted into the severed ends of the distal and proximal portions of the vas deferens. The sections are inserted a distance sufficient to place the severed ends of the vas deferens in abutting contact, around the third section 18. The angular orientation of flanges 22 and 38 allows the first and second sections 14 and 16 to be relatively easily inserted into the severed ends of the vas deferens, but limits the ability of the severed ends to pull free of stent 12 after insertion.

The confluent passages 28, 44, and 51 of stent 12 provide a conduit for the flow of sperm through the reconnected vas deferens. Flanges 22 and 38 provide a seal between the stent 12 and the connected portions of the vas deferens, preventing leakage at the anastomotic site. As shown in FIGS. 2 and 3, the second section 16 of stent 12 is proportionally larger than the first section 14 to accommodate the larger diameter of the portion of the vas deferens coming from the testicle. This dimensional difference between the first and second sections 14 and 16, along with the orientation of flanges 22 and 38 prevents the stent 12 from migrating out of the anastomotic site.

The third section 18 of stent 12 provides an anatomically correct transition zone at the anastomotic site, allowing the larger testicular portion of the vas deferens to be secured to the smaller abdominal portion without pursing or puckering at the anastomotic site. As a result, misalignment of the basement membrane and muscularis of the vas deferens is avoided. In this regard, it is preferred that the transitional surface 52 of section 18 be at an angle $\theta_5$ of 170 degrees with respect to body portion 20 and an angle $\theta_6$ of 190 degrees with respect to body portion 36.

The stent 12 is preferably made of a hydrolyzable medical plastic, allowing it to slowly break down by hydrolysis in the presence of sperm fluid. The material becomes uniformly hydrated once it is immersed in aqueous fluid. The long-chain polymeric molecules become shorter and shorter, weakening the material uniformly. The residual strength of the material as it hydrolyzes is directly related to its thickness and bulk, thus, thinner sections will crumble more quickly than thick ones. Preferred materials include polyglycolic acid and polygalactin 9-10 (e.g., manufactured by Ethicon, a division of Johnson & Johnson, under the trademark VICRYL).

The process used to produce the stent is designed to take advantage of this tendency. Specifically, the stent 12 is molded initially to have dimensions slightly greater than those desired for the finished stent 12. The stent 12 is then machined to shape the thinner flanges and tips, ensuring the desired sequential breakdown of the stent. More particularly, machining induces stresses that enhance the rapid break-up of the flanges and tips of stent 12. The bulky tubular body, however, experiences minimal stress during machining and remains stronger for a longer time.

Given the tapered nature of the flanges 22 and 38, which are thinnest at rims 34 and 50, the flange seal diameters $OD_2$ and $OD_5$ are progressively reduced after implantation. This causes a corresponding reduction in seal pressure and a movement in the maximum seal pressure points defined by rims 34 and 50 as the rims 34 and 50 are broken down. The resultant shift in the maximum seal pressure points minimizes trauma to the lining epithelium of the vas deferens.

As breakdown continues, flanges 22 and 38 and end portions 26 and 42 effectively disintegrate, allowing final tissue reorganization to occur around the relatively tubular body portions 20 and 36 of the first and second sections 14 and 16. This progression is a result of the selection of appropriate relative thicknesses for the various elements of stent 12. More particularly, the thickness $t_1$ and $t_4$ of body portions 20 and 36 is preferably twice the thickness $t_3$, $t_6$, $t_2$, and $t_5$ of end portions 26 and 42 and flanges 22 and 38. Because the progress of stent 12 breakdown is, in part, a function of thickness, end portions 26 and 42 and flanges 22 and 38 will dissolve before the body portions 20 and 36 and third section 18, thereby 38 will dissolve before the body portions 20 and 36 and third section 18, thereby providing continued support and alignment of the epithelial basement membranes at the anastomotic site where it is most required during tissue reorganization. Ultimately, even the portions 18, 20, and 36 will dissolve, leaving the fully healed vas deferens unobstructed.

While the construction and dimension of the various elements of stent 12 described above can be varied, it has been found that a particular relationship between the structure of stent 12 and the dimensions of the proximal and distal portions of the vas deferens, as determined by a sizing gauge 54, described below, provides optimal performance. More particularly, if the inner diameter of the distal (abdominal) portion of the vas deferens is designated $S_1$ and the inner diameter of the proximal (testicular) portion of the vas deferens is designated $S_2$, the dimensions of stent 12 will be as follows. $OD_1$ and $OD_4$ will be equal to 70 percent of $S_1$ and $S_2$, respectively. Similarly, $OD_2$ and $OD_4$ will be equal to 100 percent of $S_1$ and $S_2$, respectively. Dimensions $OD_3$ and $OD_6$ will be equal to 60 percent of $S_1$ and $S_2$, respectively. Dimensions $ID_1$ and $ID_2$ will be equal to 50 percent of $S_1$ and $S_2$, respectively.

The thicknesses of the body portions 20 and 36 and third section 18 of stent 12 are designated $t_1$, $t_4$, and $t_7$, as shown in FIG. 3. Preferably, $t_1$, $t_4$, and $t_7$ are equal to eight percent of $S_2$. The thicknesses of end portions 26 and 42 and the base of flanges 22 and 38, designated $t_2$, $t_3$, $t_5$, and $t_6$, preferably are equal to one half that value or four percent of $S_2$.

Turning now to the longitudinal dimensions of stent 12, the distance between flanges 22 and 38 of stent 12 is shown in FIG. 3 as the sum of $L_1$, $L_4$, and $L_7$ and is preferably equal to 425 percent of $S_1$. With this value fixed, it will be appreciated that the length of the third section 18, designated $L_7$, is a function of the transitional surface angle $\theta_5$ and the difference between the outer diameters $OD_1$ and $OD_4$ of the first and second sections 14 and 16. The remaining length between flanges 22 and 38 is attributable equally to the dimensions $L_1$ and $L_4$.

Turning to the length $L_2$ of flange 22, it will be appreciated that it is fixed by the variation between $OD_3$ and $OD_2$, given the establishment of $\theta_1$ at a preferred angle of 155 degrees. Similarly, the length $L_5$ of flange 38 is geometrically determined by the variation between $OD_5$ and $OD_6$, given the preferred establishment of angle $\theta_3$ at 155 degrees. The lengths $L_3$ and $L_6$ of end portions 26 and 42, respectively, are less than one-half of $ID_1$ and $ID_2$ to avoid occlusion by fragments of the tips on breakdown.

A stent 12 constructed in accordance with the relationships set forth above has been found to provide maximal flow of spermatic fluid through stent passages 28, 44, and 51, minimal stent bulk and length, ease of stent insertion into the vas deferens, adequate leakage protection without the application of excess pressure to the epithelium of the vas deferens, stent stability at the anastomotic site, anatomically correct tissue support surfaces at the anastomotic site, and relatively precise fitting of the stent to the vas deferens.

As will be appreciated, to provide a stent 12 that is dimensioned in accordance with the relationships set forth above, it is necessary to first measure the inner diameters $S_1$ and $S_2$ of the proximal and distal portions of the vas deferens. To accomplish this, a double-ended gauge 54 constructed as shown in FIG. 4 is employed.

More particularly, gauge 54 has a first end 56 that is used to measure the inner diameter of the distal or proximal portions of the vas deferens. A second end 58 is structured to allow the measurement of the inner diameter of the proximal (testicular) portion of the vas deferens in cases where the anastomotic site is close to the epididymus, preventing deep insertion to measure larger sizes. The ends 56 and 58 are separated by a middle section 60 which allows gauge 54 to be manipulated either manually or with the aid of surgical instruments.

Figure 4:
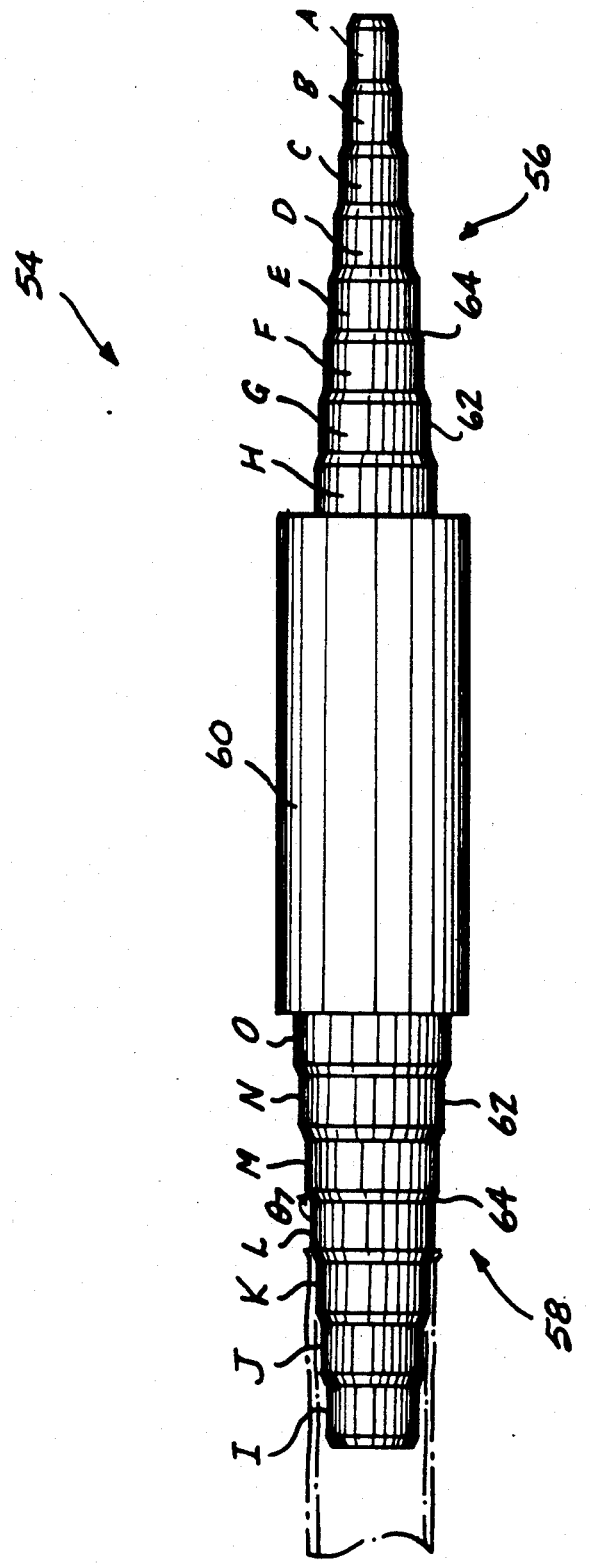
FIG. 4 is a pictorial view of a sizing gauge employed to measure the inner diameters of the testicular (proximal) and abdominal (distal) portions of the vas deferens.

As shown in FIG. 4, the first and second ends 56 and 58 of gauge 54 comprise a plurality of axially aligned, cylindrical segments 62 separated by tapered transitional sections 64. The diameters of the various segments 62 have a predetermined relationship with respect to each other. On each end 56 and 58, the segment 62 having the largest diameter is positioned adjacent the middle section 60 of gauge 54. The diameters of the remaining segments 62 become progressively smaller with distance from middle section 60.

As shown in FIG. 4, in the preferred arrangement, the first end 56 of gauge 54 includes eight segments 62 identified by reference letters A through H. The outermost segment 62 is designated A and has a diameter that is 0.005 inches (0.013 centimeters) less than the smallest expected inner diameter for the distal portion of the vas deferens. Preferably, the diameter of segment A is equal to 0.025 inches (0.06 centimeters) and each subsequent segment increases in diameter by an increment of 0.005 inches (0.013 centimeters), resulting in a diameter at segment H of 0.060 inches (0.15 centimeters). The transition between adjacent segments 62 is preferably uniform, with each transitional section 64 defining an angle $\theta_7$ of 155 degrees with respect to the preceding distal segment 62.

At the second end 58 of gauge 54, seven additional sections, designated I through O, are provided as shown in FIG. 4. The distal segment 62, designated I, has a diameter selected to correspond to the smallest expected inner diameter of the proximal (testicular) portion of the vas deferens. The diameter of the cylindrical segment 62, designated O, adjacent middle section 60 is 0.005 inches (0.013 centimeters) greater than the largest expected inner diameter of the proximal portion of the vas deferens. A uniform increment in the cylindrical segments between adjacent segments 62 is provided by the transitional sections 64, which define a 155-degree angle with respect to the preceding distal segment 62. The outer diameter of segment I is preferably 0.045 inches (0.11 centimeters) with a 0.005 inch (0.013 centimeter) incremental transition between adjacent segments resulting in a diameter at segment O of 0.075 inch (0.19 centimeters). In the preferred arrangement, the dimensions of segments E, F, G, and H on end 56 correspond to those of segments I, J, K, and L, respectively, on second end 58.

The gauge 54 is used to determine the sizes $S_1$ and $S_2$ of the abdominal and testicular portions of the vas deferens in the following manner. The appropriate end of the gauge 54 is inserted into the portion of the vas deferens to be measured, after that portion has been prepared for anastomosis. Gauge 54 is inserted until it begins to dilate the vas deferens and the vas deferens tightens around the segment 62 of gauge 54 whose diameter corresponds to the inner diameter of the vas deferens. Ultimately, the wall of the vas deferens halts the advance of the gauge 54. Because the diameters of the various segments 62 of gauge 54 are known, the inner diameter of the vas deferens can then easily be determined. As will be appreciated, the accuracy of this determination is a function of both the number of gauge segments 62 employed and the variation in diameter between adjacent segments 62. This process is repeated for both portions of the vas deferens. If a selection of stents 12 is provided having dimensions conforming to the various combinations of measured vas deferens sizes $S_1$ and $S_2$, these measurements can then be used to select an appropriately dimensioned stent 12 for use in the vasovasostomy.

With the appropriate stent 12 selected, the first and second sections 14 and 16 of the stent 12 are then inserted into the severed ends of the distal and proximal portions of the vas deferens. As a result, the severed ends of the vas deferens are placed in abutting contact adjacent the third section 18 of stent 12, in the manner described above. At this time, a surgeon reconnects the severed ends, e.g., with sutures 66, staples 68, or heat from a laser. As shown, the sutures 66 or staples 68 are spaced around the circumference of the anastomotic site and only partially penetrate the wall of the vas deferens, failing to reach the stent 12. In a preferred embodiment, sutures 66 or staples 68 are made of the same hydrolyzable medical plastic, e.g., polyglycolic acid, as stent 12, eliminating the need for their subsequent surgical removal.

The preceding discussion is focused primarily on the use of stent 12 in the performance of the surgical procedure vasovasostomy. As will be appreciated, however, stents 12 constructed in accordance with this invention can be used in anastomosis of other fluid-carrying vessels. One example of another physiological application for stent 12 is in the performance of Fallopian tube anastomosis.

Those skilled in the art will recognize that the embodiments of the invention disclosed herein are exemplary in nature and that various changes can be made therein without departing from the scope and the spirit of the invention. In this regard, and as was previously mentioned, the invention is readily embodied in various applications with various means of connection employed to the vessels. Further, it will be recognized that the dimensions and constructions of the stent can be varied in conformity with the objective set forth. Because of the above and numerous other variations and modifications that will occur to those skilled in the art, the following claims should not be limited to the embodiments illustrated and discussed herein.

The embodiments of the invention in which an exclusive property or privilege is claimed are defined as follows:

1. A stent for use in the reconnection of a severed vessel that may carry fluid and that has a first free portion and a second free portion, said stent comprising:

support means for supporting the first and second portions of the vessel, said support means having first and second sections that are insertable into the first and second free portions of the vessel, said first and second sections having first and second outer surfaces and terminating in first and second ends, respectively, said support means including a tube having an inner passage extending between said first and second ends, wherein the outer diameter of said first section of said tube is reduced at said first end and the outer diameter of said second section of said tube is reduced at said second end; and first and second flanges provided on said first and second outer surfaces of said support means, respectively, to sealably engage the first and second portions of the vessel, said first flange including a first seal surface that defines an obtuse angle with respect to said first outer surface extending toward said first end, said second flange including a second seal surface that defines an obtuse angle with respect to said second outer surface extending toward said second end, said support means and said first and second flanges being made of a material that dissolves when exposed to fluid, allowing the seal between the first seal surface and the first portion of the vessel and the seal between the second seal surface and the second portion of the vessel to vary during use of said stent to minimize trauma to the vessel.

2. The stent of claim 1 wherein the outer diameter of said first section of said tube is a first predetermined function of the inner diameter of the first portion of the vessel, the reduced outer diameter of said first end of said first section of said tube is a second predetermined function of the inner diameter of the first portion of the vessel, the outer diameter of said first flange is a third predetermined function of the inner diameter of the first portion of the vessel, the outer diameter of said second section of said tube is a fourth predetermined function of the size of the second portion of the vessel, the reduced outer diameter of said second end of said second section of said tube is a fifth predetermined function of the inner diameter of the second portion of the vessel, and the outer diameter of said second flange is a sixth predetermined function of the inner diameter of the second portion of the vessel.

3. The stent of claim 2, wherein the first and fourth predetermined functions are 70 percent, the second and fifth predetermined functions are 60 percent, and the third and sixth predetermined functions are 100 percent.

4. The stent of claim 3, wherein said first and second sections of said tube are joined by a third section that provides a uniform, gradual transition between said first and second sections.

5. The stent of claim 4, wherein the distance between said first and second flanges is a seventh predetermined function of the inner diameter of the first portion of the vessel.

6. The stent of claim 5, wherein the seventh predetermined function is 425 percent.

7. The stent of claim 6, wherein said material that said stent is made of is polyglycolic acid.

8. The stent of claim 6, wherein said material that said stent is made of is polygalactin 9-10.

9. The stent of claim 6, wherein the vessel said stent is for use with is a vas deferens.

10. The stent of claim 6, wherein the vessel said stent is for use with is a Fallopian tube.

11. A stent for use in the reconnection of a severed vessel that may carry fluid and that has a first free portion and a second free portion, said stent comprising:

support means for supporting the first and second portions of the vessel, said support means having first and second sections that are insertable into the first and second free portions of the vessel, said first and second sections having first and second outer surfaces and terminating in first and second ends, respectively; and first and second flanges provided on said first and second outer surfaces of said support means, respectively, to sealably engage the first and second portions of the vessel, said first flange including a first seal surface that defines an obtuse angle with respect to said first outer surface extending toward said first end, said second flange including a second seal surface that defines an obtuse angle with respect to said second outer surface extending toward said second end, said first and second flanges being pre-stressed, said support means and said first and second flanges being made of a material that dissolves when exposed to fluid, allowing the seal between the first seal surface and the first portion of the vessel and the seal between the second seal surface and the second portion of the vessel to vary during use of said stent to minimize trauma to the vessel.

12. A stent for use in the reconnection of a severed vessel that may carry fluid and that has a first free portion and a second free portion, said stent comprising:

support means for supporting the first and second portions of the vessel, said support means having first and second sections that are insertable into the first and second free portions of the vessel, said first and second sections having first and second outer surfaces and terminating in first and second ends, respectively, said support means including a tube having an inner passage extending between said first and second ends and wherein the outer diameter of said first section of said tube is reduced at said first end and the outer diameter of said second section of said tube is reduced at said second end; and first and second flanges provided on said first and second outer surfaces of said support means, respectively, to sealably engage the first and second portions of the vessel, said first flange including a first seal surface that defines an obtuse angle with respect to said first outer surface extending toward said first end, said second flange including a second seal surface that defines an obtuse angle with respect to said second outer surface extending toward said second end, said support means and said first and second flanges being made of a material that dissolves when exposed to fluid.

* * * * *

UNITED STATES PATENT AND TRADEMARK OFFICE
CERTIFICATE OF CORRECTION

PATENT NO. : 5,192,289
DATED : March 9, 1993
INVENTOR(S) : J. W. Jessen

It is certified that error appears in the above-identified patent and that said Letters Patent is hereby corrected as shown below:

| COLUMN | LINE | |
|---|---|---|
| 1 | 29 | delete "by" (second occurrence) |
| 5 | 31-32 | after "section 18," delete "thereby 38 will dissolve before the body portions 20 and 36 and third section 18," |
| 5 | 50 | "$OD_4$" should read --$OD_5$-- |

Signed and Sealed this

Fourth Day of October, 1994

Attest:

BRUCE LEHMAN

Attesting Officer

Commissioner of Patents and Trademarks